(12) United States Patent  
Stehle et al.

(10) Patent No.: US 7,230,701 B2
(45) Date of Patent: Jun. 12, 2007

(54) COMPACT SPECTROSCOPIC ELLIPSOMETER

(75) Inventors: Jean-Louis Stehle, Colombes (FR); Jean-Philippe Piel, Marly-le-Roi (FR); Pierre Boher, Yerres (FR); Luc Tantart, Palaiseau (FR); Jean-Pierre Rey, Fontenay aux Roses (FR)

(73) Assignee: Societe de Production et de Recherches Appliquees, Bois-Colombes (FR)

( * ) Notice: Subject to any disclaimer, the term of this patent is extended or adjusted under 35 U.S.C. 154(b) by 352 days.

(21) Appl. No.: 10/333,415

(22) PCT Filed: Jul. 16, 2001

(86) PCT No.: PCT/FR01/02305

§ 371 (c)(1), (2), (4) Date: Sep. 11, 2003

(87) PCT Pub. No.: WO02/06779

PCT Pub. Date: Jan. 24, 2002

(65) Prior Publication Data

US 2004/0070760 A1    Apr. 15, 2004

(30) Foreign Application Priority Data

Jul. 17, 2000    (FR) .................................. 00 09318

(51) Int. Cl.
*G01J 4/00*    (2006.01)

(52) U.S. Cl. ..................................... 356/369; 259/226

(58) Field of Classification Search ......... 356/364–369
See application file for complete search history.

(56) References Cited

U.S. PATENT DOCUMENTS 3,874,797 A    4/1975    Kasai (Continued)

FOREIGN PATENT DOCUMENTS

EP    0 237 415 A1    9/1987
EP    0 832 597 A1    4/1998

OTHER PUBLICATIONS

Haberland, K., et al., *Ellipsometric and reflectance-anisotropy measurements on rotating samples*, Thin Solid Films, vols. 313-314, pp. 620-624, 1998, Proceedings of the Second International Conference on Spectroscopic Ellipsometry, Charleston South Carolina, May 12-15, 1997.

(Continued)

*Primary Examiner*—Layla G. Lauchman
*Assistant Examiner*—Juan D. Valentin, II
(74) *Attorney, Agent, or Firm*—Christie, Paker & Hale, LLP

(57) ABSTRACT

The invention concerns an ellipsometer comprising: a source (2) capable of emitting a broadband ray (4), a polarizer (10) for producing a polarised incident beam (12) adapted to illuminate a sample (16) according to at least a selected angle; an analyzer (24) providing an output beam (28) in response to said reflected beam (20) and at least a reflecting optical element (14) arranged between the source (2) and the sample (16) and/or between the sample (16) and the sensor, and capable of focusing the incident beam (12) and/or the reflected beam (20) according to a selected spot The ellipsometer further comprises at least a first refracting optical element (22) arranged between the sample (16) and the sensor and/or between the source (2) and the sample (16) to collect and focus said reflected beam and/or said incident beam, thereby enabling to provide at least a refracting element (22) and a reflecting element (14) on either side of the sample (16) and hence to place the source and the sensor on the same side relative to said spot.

28 Claims, 9 Drawing Sheets

U.S. PATENT DOCUMENTS

| | | | |
|---|---|---|---|
| 5,329,357 A | 7/1994 | Bernoux et al. | |
| 5,343,293 A | 8/1994 | Berger et al. | |
| 5,546,179 A * | 8/1996 | Cheng | 356/73 |
| 5,608,526 A | 3/1997 | Piwonka-Corle et al. | |
| 5,646,733 A * | 7/1997 | Bieman | 356/604 |
| 5,764,365 A | 6/1998 | Finarov | |
| 5,793,480 A * | 8/1998 | Lacey et al. | 356/73 |
| 5,805,285 A | 9/1998 | Johs et al. | |
| 5,859,424 A * | 1/1999 | Norton et al. | 250/226 |
| 5,910,842 A * | 6/1999 | Piwonka-Corle et al. | 356/369 |
| 5,963,327 A | 10/1999 | He et al. | |
| 5,969,818 A | 10/1999 | Johs et al. | |
| 6,031,614 A | 2/2000 | Michaelis et al. | |
| 6,091,499 A * | 7/2000 | Abraham et al. | 356/623 |
| 6,153,444 A * | 11/2000 | Nakano et al. | 438/16 |
| 6,184,984 B1 * | 2/2001 | Lee et al. | 356/369 |
| 6,268,916 B1 * | 7/2001 | Lee et al. | 356/369 |
| 6,469,788 B2 * | 10/2002 | Boyd et al. | 356/369 |
| 6,611,330 B2 * | 8/2003 | Lee et al. | 356/369 |
| 6,804,003 B1 * | 10/2004 | Wang et al. | 356/369 |
| 6,856,384 B1 * | 2/2005 | Rovira | 356/73 |

OTHER PUBLICATIONS

Hazebroek, H.F., et al., *Automated laser interferometric ellipsometry and precision reflectometry*, J. Phys. E: Sci. Instrum., vol. 16, pp. 654-661, 1983.

International Search Report of PCT/FR01/02305, dated Nov. 23, 2001.

Internal Preliminary Examination Report of PCT/FR01/02305, dated May 31, 2002.

* cited by examiner

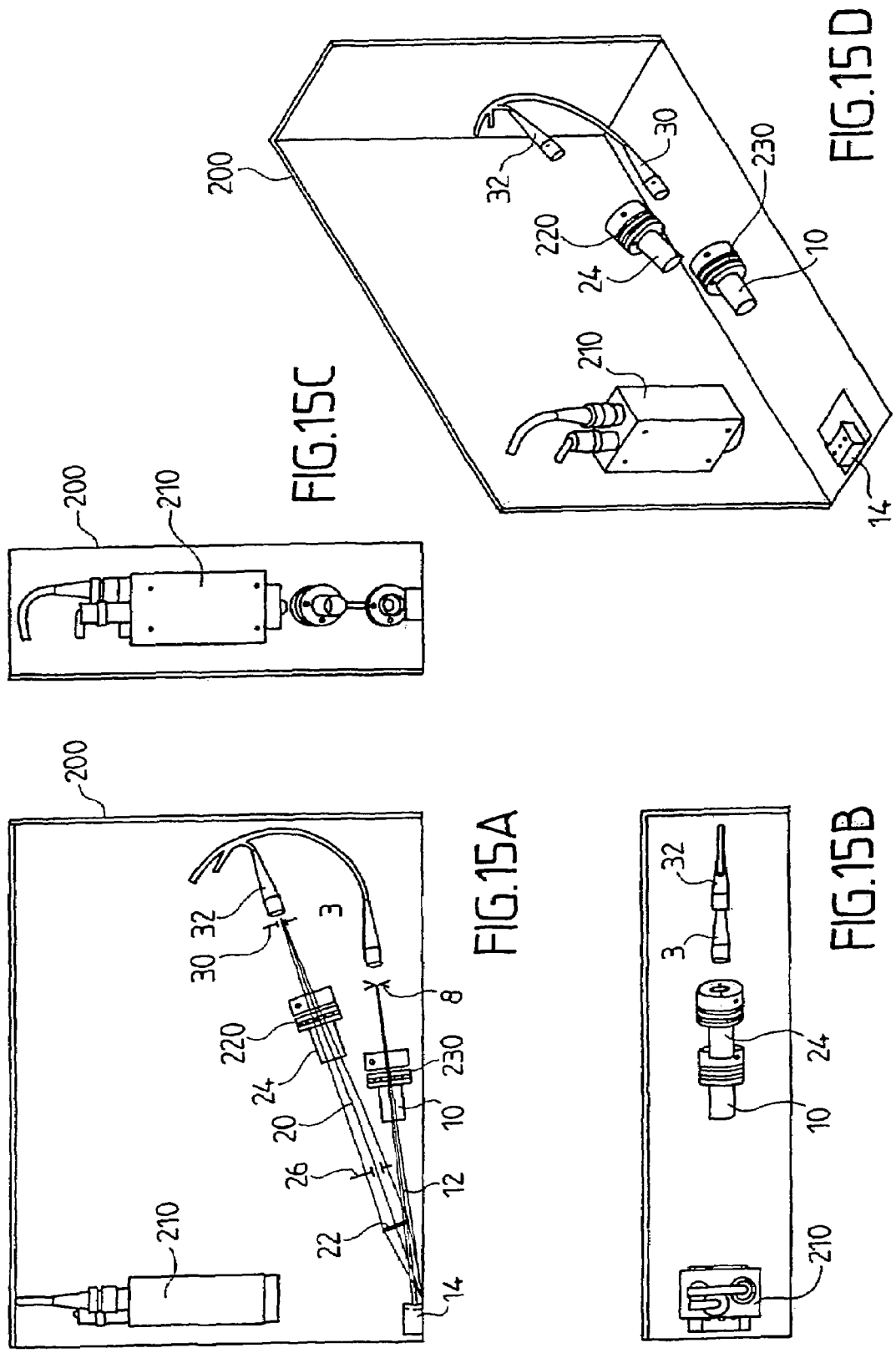

COMPACT SPECTROSCOPIC ELLIPSOMETER

CROSS-REFERENCE TO RELATED APPLICATION

This application is a National Phase Patent Application of International Application Number PCT/FR01/02305, filed on Jul. 16, 2001, which claims priority of French Patent Application Number 00/09318, filed Jul. 17, 2000.

The present invention relates to a spectroscopic ellipsometer.

Ellipsometry is a non-destructive optical measuring technique which consists of comparing the state of polarisation of an incident beam illuminating a sample with the state of polarisation of the beam reflected by the said sample with a view to deducing therefrom information concerning the properties of the layers and materials which constitute the said sample.

Numerous spectroscopic ellipsometry assemblies are already known.

For example, in U.S. Pat. No. 5,608,526 a spectroscopic ellipsometer comprises a source emitting a broadband light beam which is polarised by a polariser in order to produce a polarised incident beam intended to illuminate the sample. An analyser receives the beam reflected by the sample thus illuminated and produces an output beam in response to this reflected beam. A detector converts the output beam into a signal capable of being processed by processing means in order to determine the changes of phase and of amplitude of the state of polarisation of the output beam caused by the reflection of the polarised incident beam on the sample.

In this ellipsometer all the optical elements which are placed between the polariser and the analyser are optical elements of the reflector type, with a small angle of incidence relative to the normal.

Such an ellipsometer is satisfactory. Nevertheless, the applicants have set themselves the problem of further improving this ellipsometer, particularly with regard to the compactness, the transmission of the incident and/or reflected beams, and in particular the transmission of the state of polarisation of the incident and/or reflected beams.

The present invention provides just such a solution to this problem.

It relates to a spectroscopic ellipsometer comprising:
  a source capable of emitting a broadband light beam;
  a polariser to polarise the broadband light beam and to produce a polarised incident beam capable of illuminating a sample according to at least one chosen angle of incidence;
  an analyser to receive the beam reflected by the sample thus illuminated and to produce an output beam in response to this reflected beam;
  a detector to convert the output beam into an output signal;
  processing means to process the output signal from the detector and to determine the changes of phase and of amplitude of the state of polarisation of the output beam caused by the reflection of the polarised incident beam on the sample; and
  at least one reflecting optical element disposed between the source and the sample and/or between the sample and the detector in order to focus the incident beam and/or the reflected beam according to a chosen spot.

According to a general definition of the invention, the ellipsometer further comprises at least one first refracting optical element disposed between the sample and the detector and/or between the source and the sample in order to collect and to focus the said reflected beam and/or the said incident beam.

The fact that according to the invention a refracting element and a reflecting element are placed on either side of the sample makes it possible to ensure that the source and the detector are disposed on the same side with respect to the spot on the sample, which significantly reduces the dimensions of the ellipsometer.

Furthermore, relative to the spectroscopic ellipsometers according to the prior art, particularly with regard to U.S. Pat. No. 5,608,526, the ellipsometer according to the invention makes it possible to improve the transmission of the incident and/or reflected beam, to avoid any effect of change of phase on the polarisation of the incident and/or reflected beam, and to improve the compactness and the stability of the ellipsometer.

According to a first embodiment of the ellipsometer according to the invention, a first optical fibre connects the analyser to an optical device of the type belonging to the group formed by a detector, a spectrograph, a spectrometer, and the like.

The ellipsometer according to the invention further comprises a second refracting optical element disposed between the analyser and the inlet of the first optical fibre, the second refracting optical element being capable of focusing the output beam emitted by the analyser into the inlet of the first optical fibre.

Such a second refracting optical element has the advantage that it permits the adaptation of the output beam emitted by the analyser to the inlet of the optical fibre and, if the case arises, to compensate for a difference in depth (that is to say in Z, in the case of an orthonormal co-ordinate system XYZ) on the sample.

According to a second embodiment of the ellipsometer according to the invention, a second optical fibre connects to the source to the polariser.

In practice, the first and/or the second refracting optical element is a simple or compound transmission lens, preferably comprising a minimal polarising effect and capable of forming an achromatic assembly with the associated optical units. Moreover, the refracting optical units can have an anti-reflecting coating in order to improve the optical transmission of the system.

According to another aspect of the invention the first refracting optical element comprises an aperture capable of allowing the polarised incident beam to pass towards the sample and of collecting the reflected beam in order to focus it onto the analyser.

According to another characteristic of the invention, the ellipsometer further comprises a compensating optical element disposed between the polariser and the analyser, upstream or downstream of the sample according to the direction of propagation of the light. Such a compensating optical element can be achromatic, rotatable and/or removable.

According to yet another characteristic of the invention the ellipsometer according to the invention also comprises a blocking optical element disposed downstream of the polariser according to the direction of propagation of the light in order to eliminate stray radiation emitted by the source and the polariser, and to keep the image of the source fixed, without the deviation, the deflection and the chromatic aberration of the polariser.

Advantageously the polariser and the optical elements associated with the said polariser as well as the analyser and the optical elements associated with the said analyser are placed in one and the same optical head, which further improves the compactness of the ellipsometer according to the invention.

The optical head is preferably movable in translation according to the axis X and/or Y so that the incident beam on the sample is displaced longitudinally and/or laterally.

The optical head is advantageously movable on the Z axis so that the incident beam on the sample is displaced in height.

In practice, the ellipsometer comprises a sample holder which is fixed and/or movable in X, Y and/or Z and/or in rotation about an axis in Z.

According to another aspect of the invention, the ellipsometer comprises a window disposed in a plane substantially parallel to the surface of the sample and through which the incident beam and the reflected beam pass with oblique incidence.

Other characteristics and advantages of the invention will become apparent in the light of the following detailed description and the drawings, in which:

FIGS. 15A to 15D show schematically an optical head containing the analyser, the polariser and the associated optical units, but the means for fixing the different elements are not shown.

The drawings include elements of a definite nature. These will serve to aid understanding of the invention and to define it, as appropriate.

Figure 1:
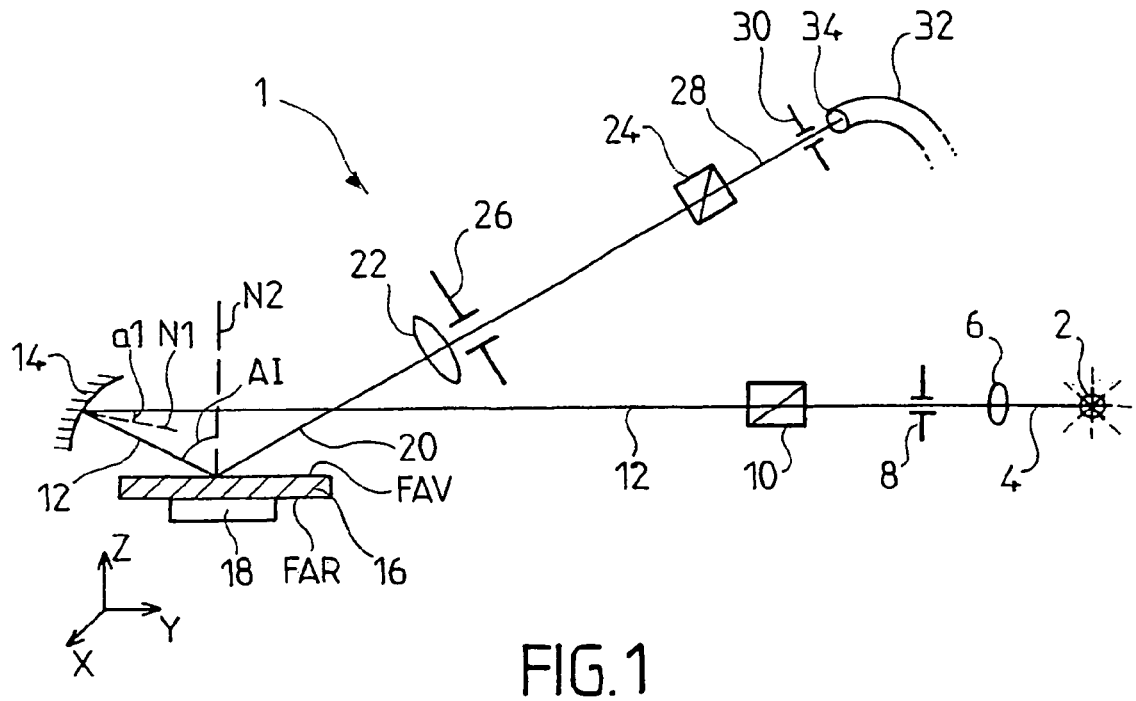
FIG. 1 shows schematically an ellipsometer having a reflecting element disposed between the polariser and the sample and a refracting element disposed between the sample and the analyser according to the invention.

With reference to FIG. 1, an ellipsometer 1 according to the invention comprises a source 2 emitting a broadband light beam 4. The source 2 is for example a xenon arc lamp which emits radiation with broadband frequency components in the ultraviolet, visible and/or the near infrared.

As a variant, the source may be tungsten lamp combined with a deuterium lamp in order to cover a spectral range substantially similar to that of the xenon lamp.

According to a first embodiment of the invention, the broadband light beam 4 is propagated in a polariser 10 after having been focused by focusing means 6 and delimited by an entry slot 8. The light beam 12 which leaves the polariser 10 is a polarised incident beam which constitutes the measurement beam with a known state of polarisation.

The polariser 10 preferably has a circular aperture in order to limit the size of the polarised incident beam so as to prevent the two states of polarisation from overlapping. The diameter of the circular aperture of the polariser is of the order of 1 mm and the distance between the slot 8 and the polariser 10 is of the order of 50 mm.

As a variant (FIG. 2), the beam 4 emitted by the source 2 can be routed through the polariser 10 via an optical fibre 3.

Under these conditions the source 2 can advantageously be offset, as will be described in greater detail below.

Figure 2:
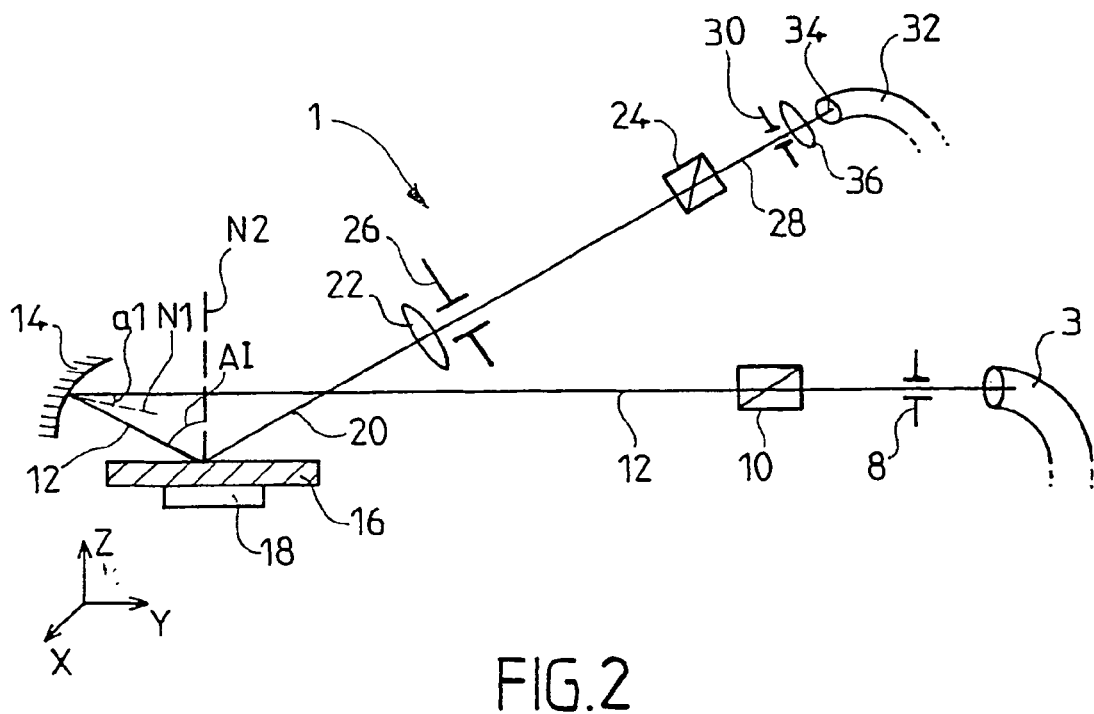
FIG. 2 shows schematically the ellipsometer of FIG. 1 with an optical fibre routing the illuminating beam emitted by the source towards the sample.

With reference to FIG. 1 or FIG. 2, the polarised incident beam 12 strikes a mirror 14 with an angle aI of low incidence (that is to say close to the normal N1 to the reflecting surface of the mirror 14). The mirror 14 is for example an elliptical mirror. The mirror 14 projects the image of the entry slot 8 according to a small spot (for example 25µ×25µ, of square shape) on the sample 16. The polarised incident beam 12 is projected on the sample 16 at a greater angle of incidence AI with respect to the normal N2 of the sample.

For example, the numerical aperture of the mirror 14 is of the order of 0.15° and the angle of incidence AI of the polarised incident beam 12 with respect to the normal N2 to the sample 16 is of the order of 63.5° to 80.5°.

The sample 16 is for example produced from a semiconductor material with at least one thin layer deposited on a transparent substrate. The sample comprises a front face FAV which receives the incident beam and a rear face FAR in contact with the sample holder. The invention quite clearly has an application for samples of types and produced from any material.

The sample 16 is disposed on a sample holder 18. The sample holder 18 may be fixed and/or movable in an orthonormal co-ordinate system according to the axes X, Y, Z and/or movable in rotation. The sample holder may equally be suspended.

According to another embodiment of the invention (FIG. 3), the ellipsometry measurement is achieved through a window or port 19, as described in the French application filed on 26 May 2000 under the number 00 06771 by the present applicants and entitled "Method and apparatus for ellipsometric metrology for sample contained in a chamber or the like".

The window 19 is disposed in a plane substantially parallel to the surface of the sample 16. For example, the window 19 at least partially closes the chamber (not shown) in which the sample is disposed. For example, the window 19 is made from a material of the silica type which is isotropic and transparent in the ultraviolet.

The incident beam 12 and reflected beam 20 pass through the window with oblique incidence.

Figure 3:
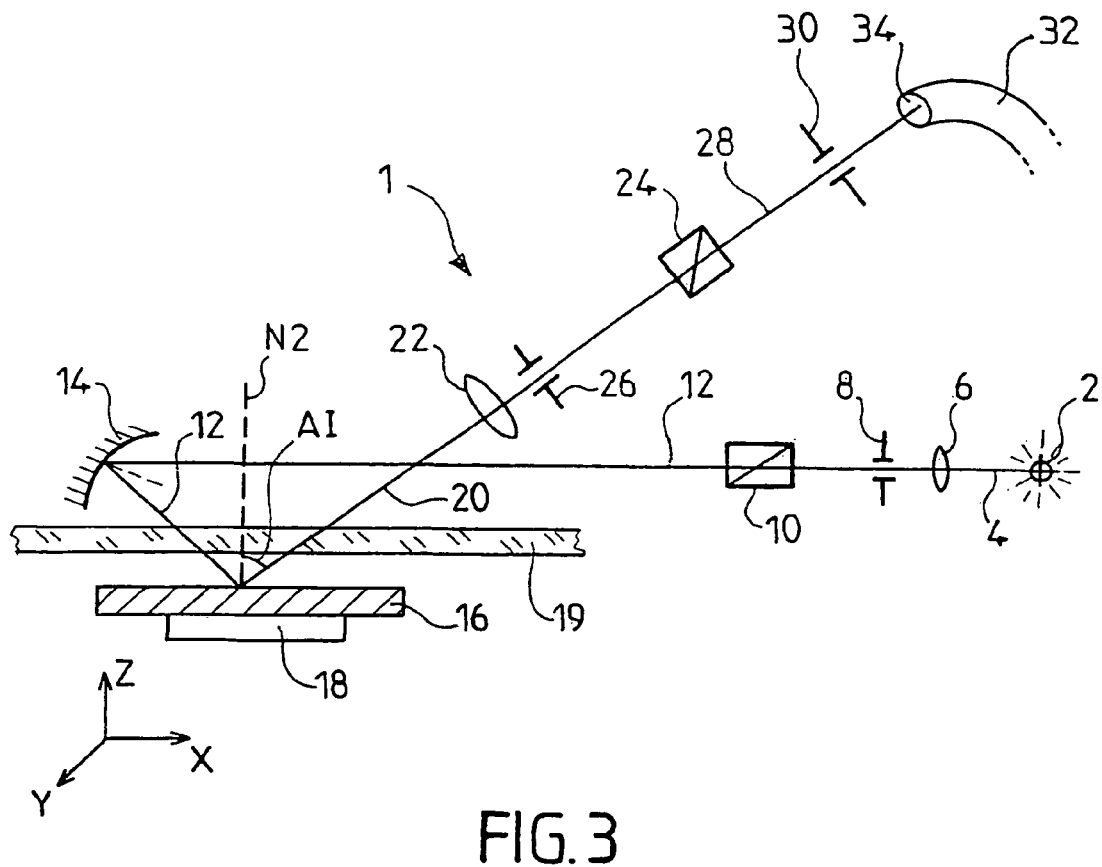
FIG. 3 shows schematically the ellipsometer of FIG. 1 with an ellipsometry measurement produced through a window according to the invention.

With reference to at least any one of FIGS. 1 to 3, a refracting (or transmitting) optical element 22 receives the beam 20 reflected by the sample (if appropriate via the window 19). This refracting optical element 22 then focuses the reflected beam 20 through an analyser 24.

The fact that according to the invention a refracting element and a reflecting element are placed on either side of the sample makes it possible to ensure that the source and the detector are disposed on the same side with respect to the spot on the sample, which significantly reduces the dimensions of the ellipsometer.

Furthermore, relative to U.S. Pat. No. 5,608,526, the refracting optical element 22 replaces the collecting mirror and the following mirror disposed between the sample and the analyser. Therefore by virtue of the refracting optical element 22, the spectroscopic ellipsometer according to the invention is more compact and the transmission of the incident and/or reflected beam, particularly the transmission of the state of polarisation of the reflected beam, is improved in so far as the transmitting lenses minimise the effects of change of phase of the polarisation which are generally produced by the reflecting elements.

In practice a blocking element of the slot type 30 is provided downstream of the analyser 24. This slot 30 may be that of a spectrometer (not shown).

As a variant the beam 28 emitted by the analyser 24 is routed into an optical fibre 32 via the slot 30.

The aperture of the slot 30 is preferably adapted to the inlet 34 of the optical fibre 32.

A blocking optical element of the slot type 26 is preferably disposed downstream of the refracting optical element 22 according to the direction of propagation of the light in order to block certain radiations reflected by the sample.

The width of the slot 26 determines the angles of incidence associated with the beam reflected by the sample and the arrangement of the centre of the slot determines the mean angle of incidence associated with the measurement of the reflected beam.

Actuating means (not shown) are preferably provided in order to control the width of the slot 26 as well as the arrangement of the centre thereof.

In certain embodiments the width and the centre of the slot 26 are fixed.

Figure 4:
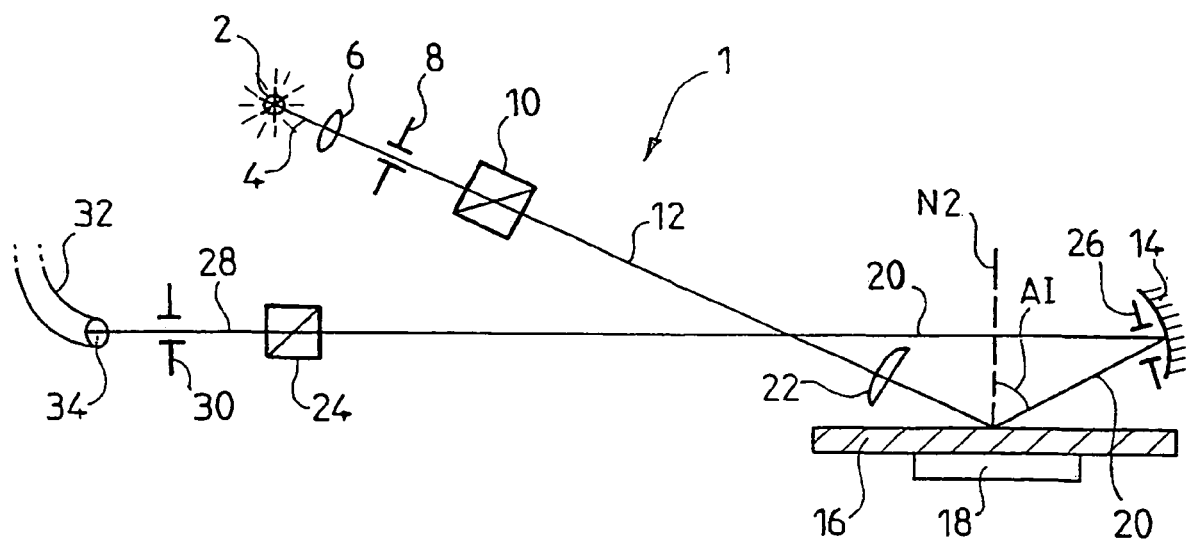
FIG. 4 shows schematically a spectroscopic ellipsometer having a refracting element disposed between the polariser and the sample and a reflecting element disposed between the sample and the analyser according to the invention.

With reference to FIG. 4, a variant of the spectroscopic ellipsometer of FIG. 1 is shown in which the refracting/transmitting optical element 22 is disposed in the outward path (that is to say between the polariser and the sample) to the location where it is placed in the return path (that is to say between the sample and the analyser).

The elements 2, 4, 6, 8 and 10 of the ellipsometer of FIG. 1 are shown in FIG. 4. The polarised incident beam 12 is focused onto the sample 16 through the refracting/transmitting optical element 22 at a raised angle of incidence AI with respect to the normal N2 of the sample (for example 71°).

The reflected beam 20 is collected by the mirror 14 so that it is then directed towards the analyser 24.

The blocking element 26 is disposed close to the mirror 14 in order to define the radiations of the reflected beam 20 intended to be analysed by the analyser 24.

There, too, the refracting element 22 and the reflecting element 14 are disposed on either side of the sample in such a way as to place the illuminating arm and the analysing arm of the ellipsometer on the same side.

Figure 5:
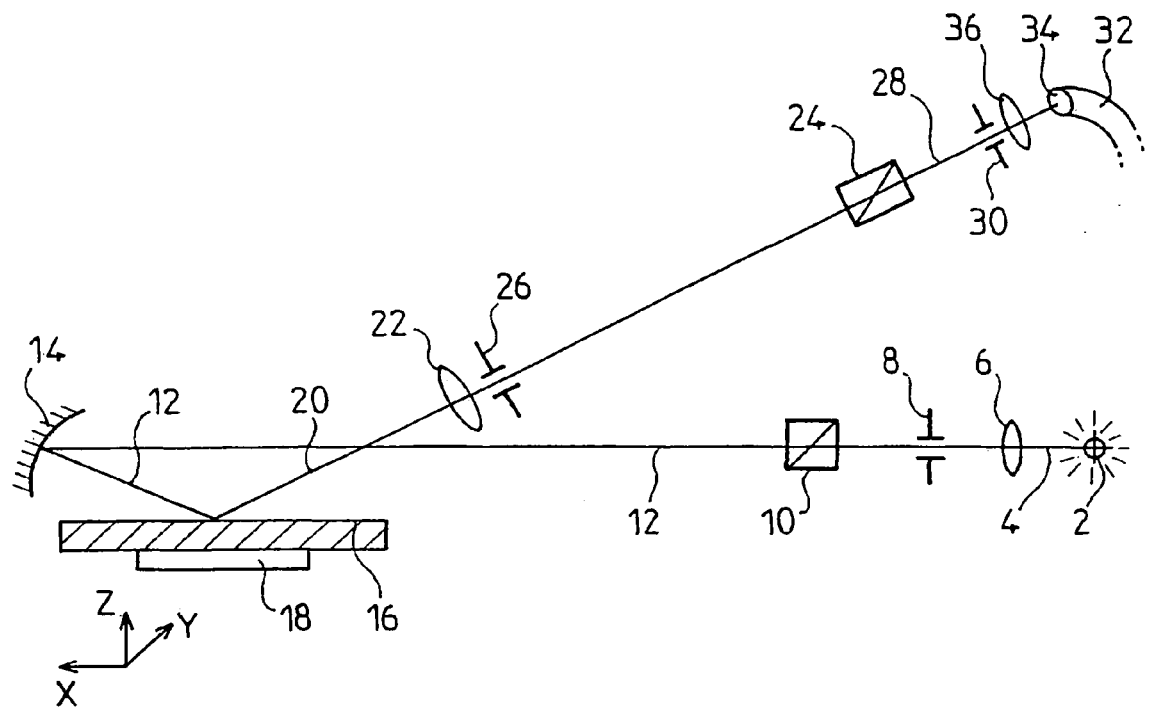
FIG. 5 shows schematically the ellipsometer of FIG. 1, to which is added another refracting element disposed between the analyser and the inlet of the optical fibre according to the invention.

With reference to FIG. 5, a variant of the ellipsometer of Figure is shown in which another refracting/transmitting optical element 36 is disposed between the analyser 24 and the inlet 34 of the optical fibre 32. This refracting/transmitting optical element 36 focuses the output beam 28 emitted by the analyser into the inlet 34 of the optical fibre 32. Such a refracting/transmitting optical element 36 has the advantage that it permits the adaptation of the output beam emitted by the analyser to the inlet of the optical fibre, and thus, if the case arises, of compensating for a difference in depth (that is to say in Z, in the case of an orthonormal co-ordinate system XYZ) on the sample.

The refracting/transmitting optical element 36 and/or 22 is preferably a simple or compound transmission lens, preferably comprising a minimal polarising effect, when it is compound, the lens 22 or 36 forms an achromatic assembly with its associated optical units. Moreover, the refracting optical units can have an anti-reflecting coating in order to improve the optical transmission of the system. The refracting/transmitting optical element 22 can be defined according to an opening capable of allowing the incident beam 12 emitted by the polariser to pass through towards the sample and to collect the reflected beam 20 emitted by the sample in order to focus it towards the analyser 24.

Figure 6:
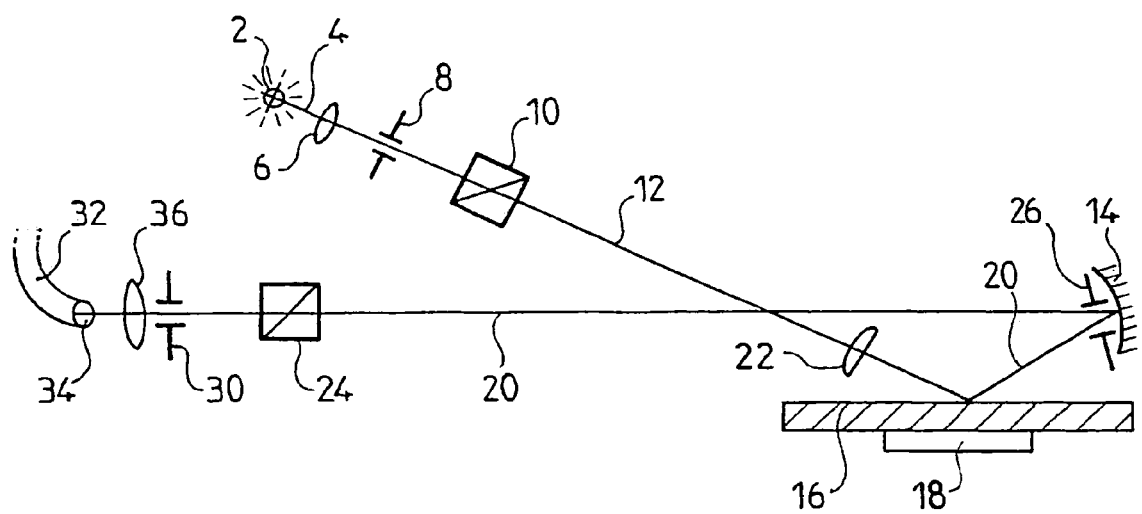
FIG. 6 shows schematically the ellipsometer of FIG. 4, to which is added another refracting element disposed between the analyser and the inlet of the optical fibre according to the invention.

With reference to FIG. 6, a variant of the ellipsometer described with reference to FIG. 4 is described in which a transmitting lens 36 has been introduced between the slot 30 and the inlet 34 of the optical fibre 32.

Figure 7:
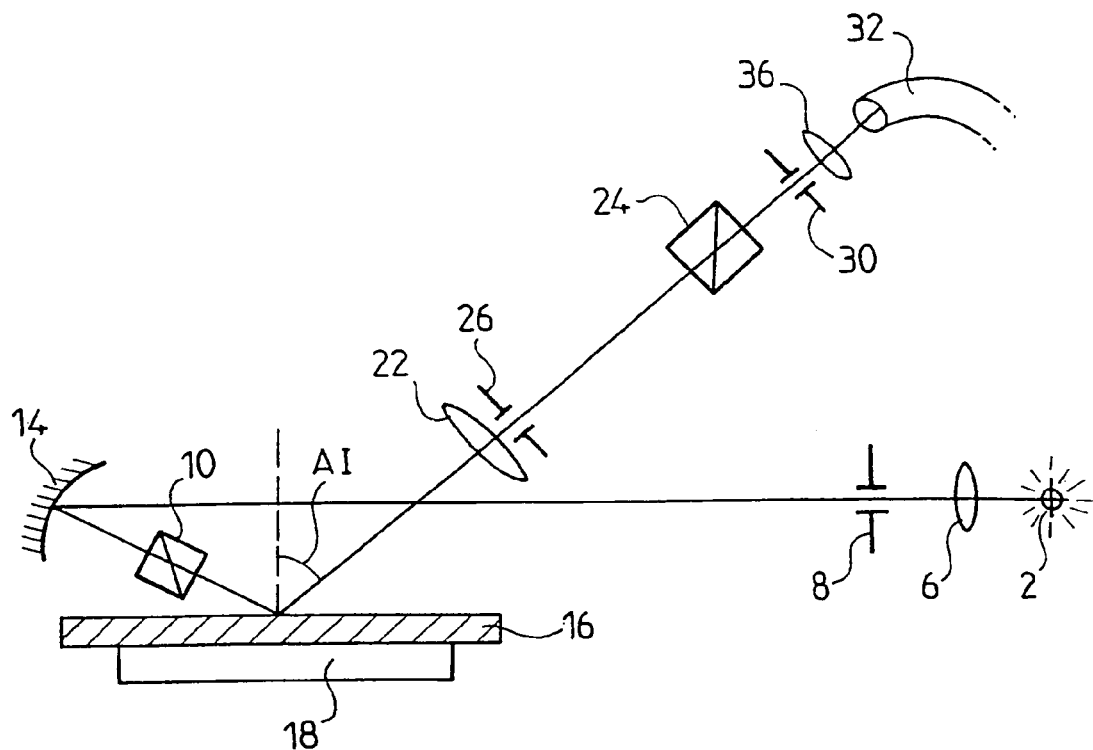
FIG. 7 shows an ellipsometry assembly according to the invention in which the polariser is disposed between the reflecting element and the sample.

With reference to FIG. 7, a variant of the ellipsometer of FIG. 1 is shown in which the polariser 10 is placed between the mirror 14 and the sample 16. This arrangement can quite obviously be used in combination with the variants described in the other figures.

Figure 8:
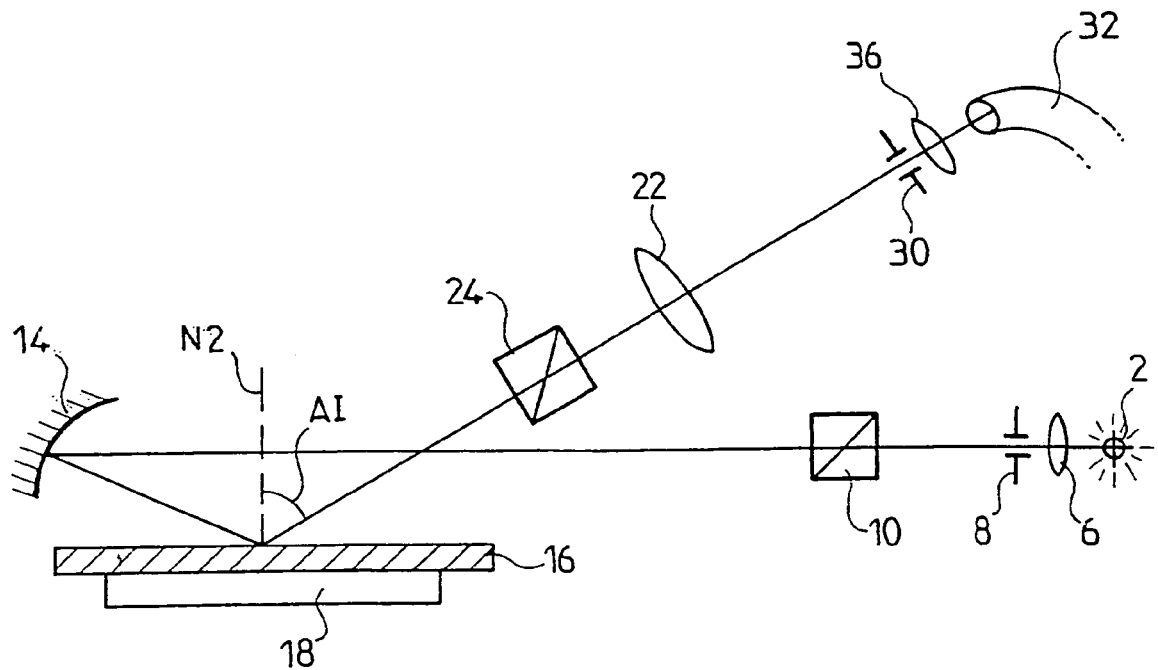
FIG. 8 shows an ellipsometry assembly according to the invention in which the analyser is placed upstream of the refracting element.

With reference to FIG. 8, another variant of the ellipsometer according to the invention is shown in which the lens 22 is disposed downstream of the analyser 24 according to the direction of propagation of the light. This arrangement, like the others, can quite obviously be used in combination with the variants described in the other drawings.

Figure 9:
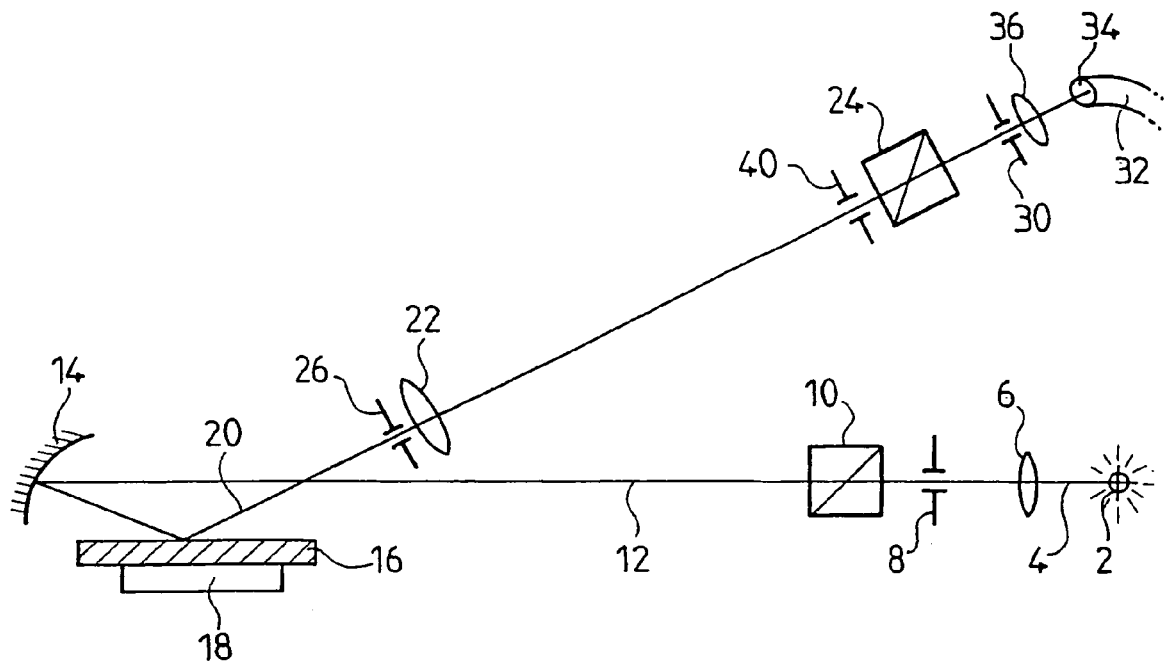
FIG. 9 is a diagram showing a variant in which a blocking element is placed upstream of the refracting element placed between the sample and the analyser according to the invention.

With reference to FIG. 9, another variant of the ellipsometer described with reference to FIG. 5 is shown. In this variant, the blocking element is disposed upstream (according to the direction of propagation of the light) of the transmitting lens 22 instead of being disposed downstream as in the ellipsometer of FIG. 5. Furthermore, a blocking element 40 is disposed upstream of the analyser 24.

The blocking elements 26 and 40 as well as 30 permit blocking of the reflected beam in an optimal manner.

Figure 10:
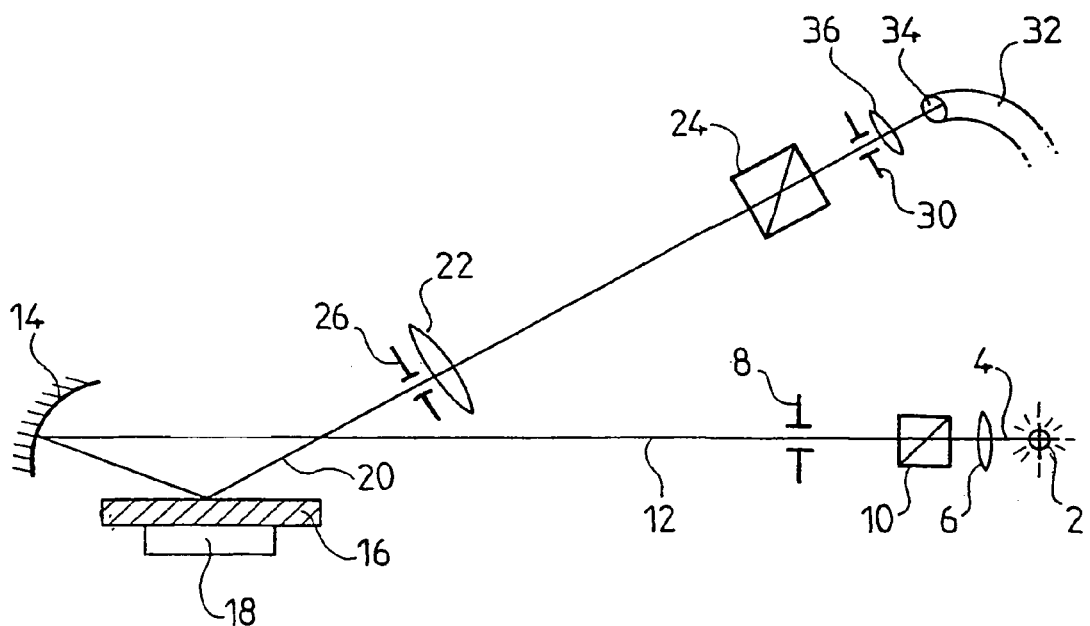
FIG. 10 is a diagram showing a variant in which a blocking element is placed downstream of the polariser according to the invention.

With reference to FIG. 10, another variant of the spectroscopic ellipsometer is described in which, by comparison with the ellipsometer of FIG. 9 the blocking element 40 has been eliminated and the blocking element 8 is disposed downstream of the polariser 10 instead of being placed upstream as with reference to FIG. 9.

The arrangement of the blocking element 8 downstream of the polariser according to the direction of propagation of the light makes it possible to eliminate the stray radiation emitted by the source and by the polariser and to keep the image of the source fixed without the deviation, the deflection and the chromatic aberration of the polariser.

Figure 11:
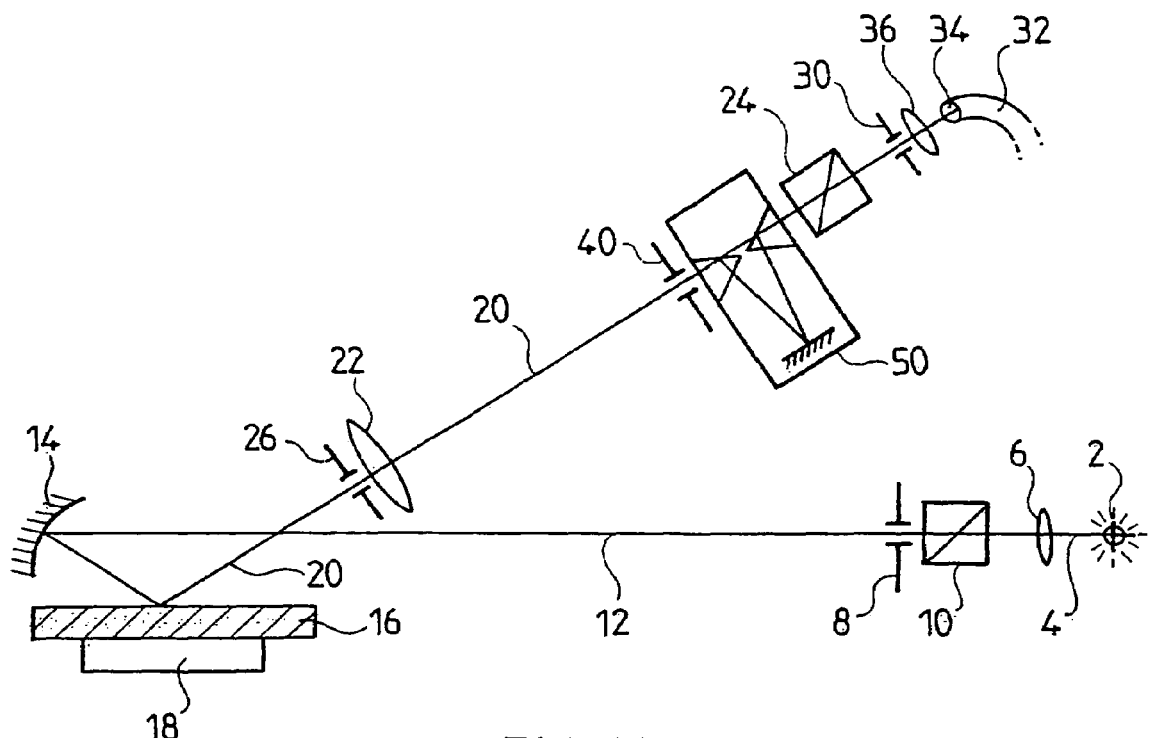
FIG. 11 is a diagram showing a variant in which a compensating element is placed upstream of the analyser according to the invention.

With reference to FIG. 11, another variant of the spectroscopic ellipsometer according to the invention is shown. In this variant, by comparison with that described with reference to FIG. 10, upstream of the analyser 24 there is disposed a blocking element 40 followed by a compensator

50. The compensating element 50 comprises a mirror. The function of the compensating element 50 is to turn the phase of the polarised light of a known value in order to place it in optimal measuring conditions regardless of the nature of the sample measured.

Figure 12:
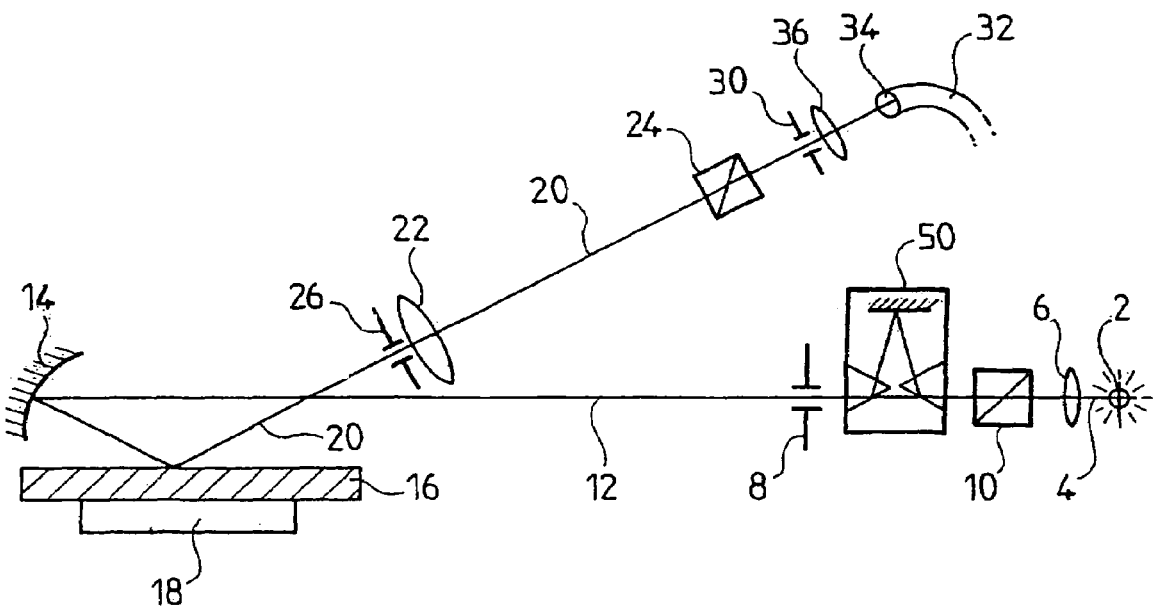
FIG. 12 is a diagram showing a variant in which a compensating element is placed downstream of the polariser according to the invention.

With reference to FIG. 12, another variant of the spectroscopic ellipsometer according to the invention is shown in which a compensating element 50 is disposed between the polariser 10 and the blocking element 8.

Figure 13:
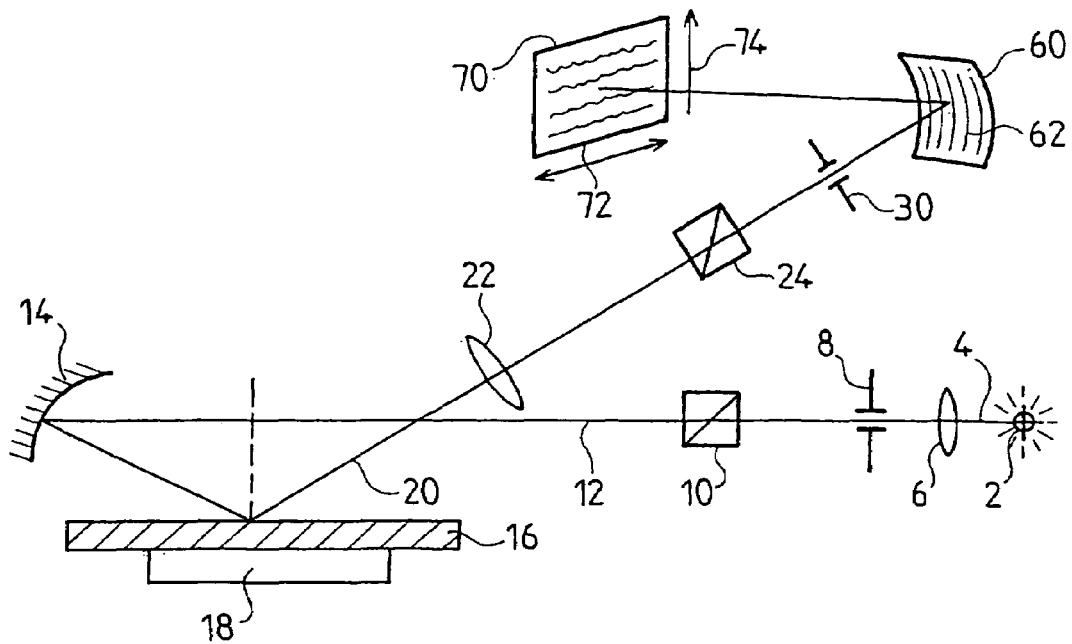
FIG. 13 shows schematically a variant in which an array ensures a crossed spectral dispersion in accordance with the angle of incidence according to the invention.

With reference to FIG. 13, a variant of the ellipsometer according to the invention is shown in which a function of crossed dispersion of wavelength/angle of incidence AI is produced by means of an array 60 disposed downstream of the slot 30 according to the direction of propagation of the light. The array 60 comprises vertical lines 62 which make it possible to produce a horizontal spectral dispersion 72 on a detector 70 of the CCD matrix type and a vertical dispersion according to the angle of incidence 74.

In the embodiment according to FIG. 13, slots are not provided in order to take all the angles of incidence since this function is provided by the array 60 and the matrix detector 70. Quite clearly, on the source side it is possible to use an optical fibre in order to offset the said source. Equally, it is possible to offset on the detection side the elements such as the array, the detector, the spectrograph, etc. with the aid of an optical fibre.

Figure 14:
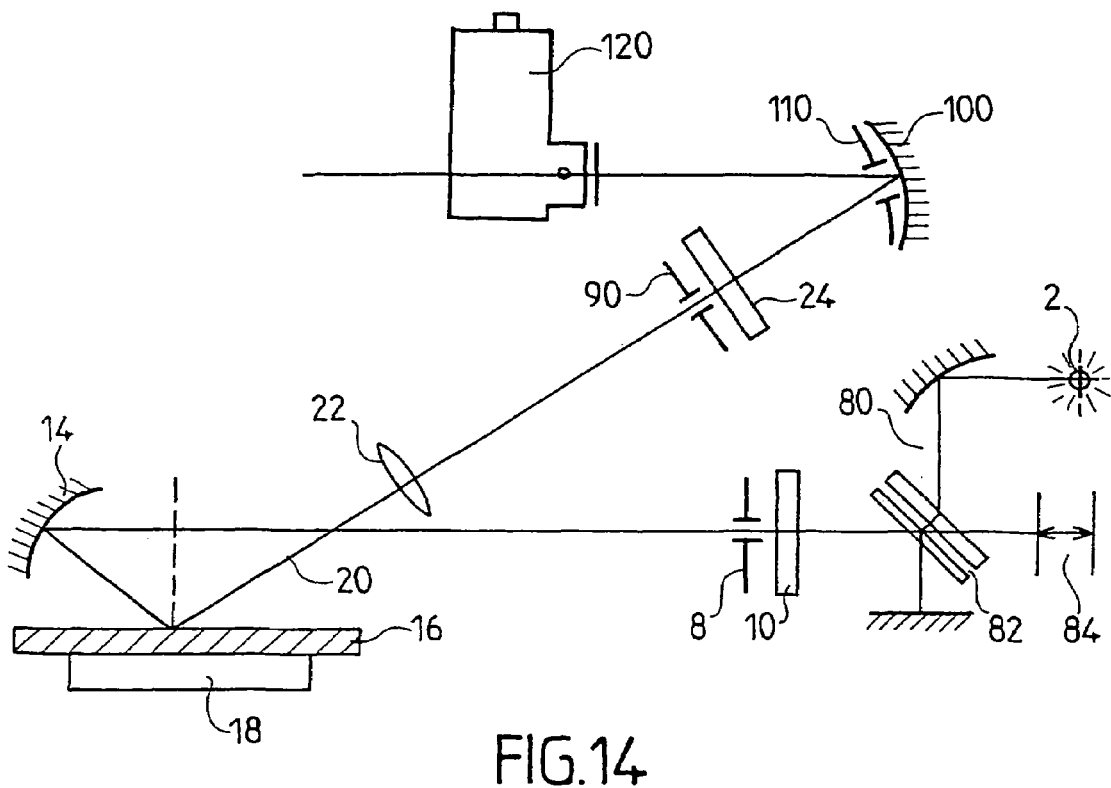
FIG. 14 is an ellipsometry assembly function in the infrared according to the invention.
Figure 16A:
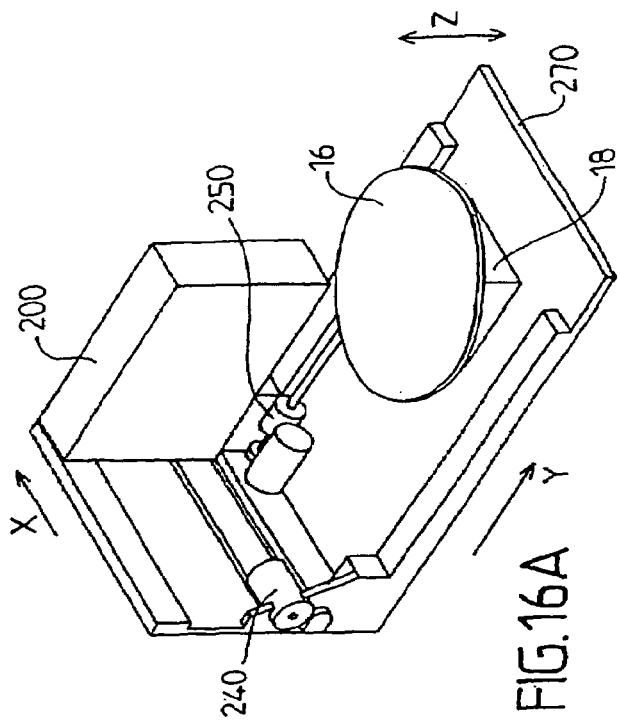
FIGS. 16A to 16D illustrate the displacement of the optical head according to the invention.
Figure 16B:
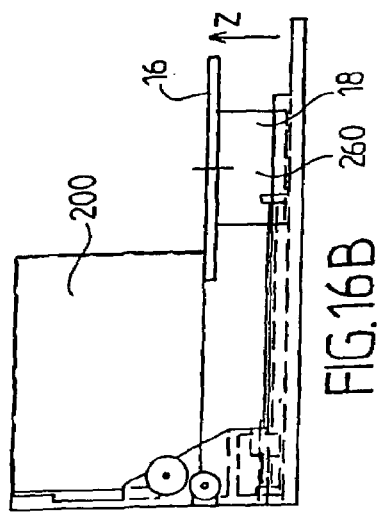
Figure 16C:
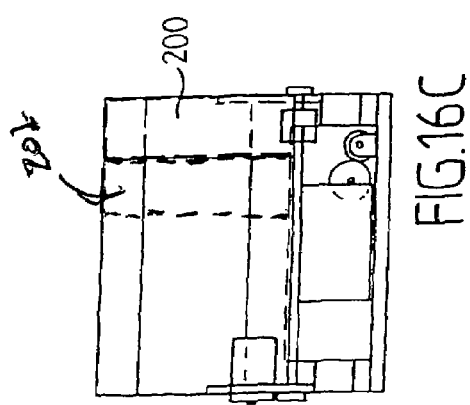
Figure 16D:
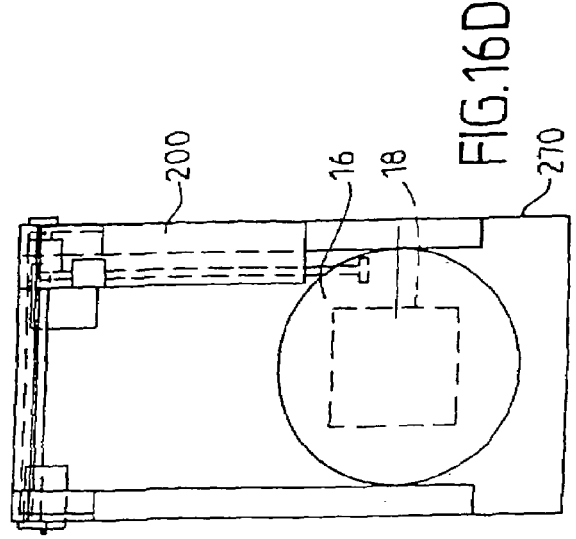

With reference to FIG. 14, an ellipsometric assembly according to the invention is shown in which the source 2 is capable of emitting in the infrared.

The assembly provides an interferometer 80 of the Michelson type. The interferometer 80 comprises at least one mirror 82 which is movable to order 84.

The polariser 10 here is of the type with a grid and compatible in IR.

On the detection side there are provided a lens 22, an analyser 24 preferably with a grid ad a slot 90 disposed upstream of the analyser 24. The slot 90 is of the cutter or blocking element type in order to eliminate the stray reflections from the rear face of the sample, as described with reference to the French application filed by the present applicants on 17 Jul. 2000 under the number 00 09318 and entitled "High spatial resolution infrared ellipsometer".

In this assembly the detector 120 is preferably a detector of the mercury-cadmium-tellurium, liquid nitrogen or the like type and is preferably compatible with operation in the infrared.

A mirror 100 advantageously focuses the beam emitted by the analyser 24 onto the detector 120. A device 110 for selecting angles of incidence is preferably coupled to the mirror 100 in order to select, for the measurements by the detector, only the radiation reflected by the sample under oblique incidence within a chosen range of angles of incidence.

In the assemblies described with reference to FIGS. 1 to 14, the refracting and reflecting elements 22 and 14 respectively are advantageously disposed on either side of the sample in order to dispose the source and the detector on the same side with respect to the spot on the sample, in order in particular to reduce the dimensions of the ellipsometer and thus to offer a saving of space and of weight.

Moreover, the use of optical fibres on the source side and/or on the detection side also makes it possible to offset the optical arrangements at a distance and to create multiplexes easily, which also offers a saving of time.

Furthermore, the applicants have observed that by disposing the illuminating arm and the analysing arm on the same side with respect to the sample, the said illuminating and analysing arms can be disposed in one and the same optical head accommodated in an ellipsometry box capable of being displaced according to the axes X, Y and/or Z.

With reference to FIGS. 15A to 15D, these show such an optical head 200 containing the illuminating and analysing arms of a spectroscopic ellipsometer according to the invention. The head or box 200 is of generally parallelepipedal shape, for example 200 mm in height, 315 mm in length and 83 mm in width. The box 200 advantageously further comprises a camera 210 intended to be disposed on the normal to the sample.

The transmitting lens 22 preferably comprises an aperture adapted to allow the polarised incident beam 12 to pass through towards the sample, and to collect/focus the reflected beam through the analyser 24.

The polariser 10 and the associated elements of the illuminating arm are placed in a first support 230. The support 230 is placed relative to the sample and to the mirror 14 in such a way as to produce an ellipsometry measurement as taught with references to FIGS. 1 to 14. The support 230 is fixed in the box with the aid of appropriate fixing means.

Likewise, the analyser 24 and the associated elements of the analysing arm are placed in a second support 220. The support 220 is placed relative to the sample and the lens 22 in such a way as produce an ellipsometry measurement as taught with references to FIGS. 1 to 14. The support 220 is fixed in the box with the aid of appropriate fixing means.

In practice, the support 230 comprise the polariser 10 and the blocking element 8. The illuminating arm is advantageously connected to the source 2 via an optical fibre 3 accommodated in the interior of the box and of which one of the ends is connected to the source thus disposed on the exterior of the box 200.

In practice, the support 220 comprises the analyser 24, the blocking element 26, the blocking element 40 and the lens 36. The spectrometer (not shown) is preferably disposed on the exterior of the box and connected to the support 230 by an optical fibre 32.

Equally, the detector and the processing means (not shown) are disposed on the exterior of the box 200 and connected to the box via the optical fibres 3 and 32.

With reference to FIGS. 16A to 16D, the box 200 is movable in translation according to the axes X, Y, and/or Z in order to displace the incident beam on the sample longitudinally, laterally and/or vertically.

On its side the sample holder 18 can be kept fixed. The sample holder 18 is also preferably movable in translation in X, Y and/or Z. Moreover, the sample holder is capable of being movable in rotation about a vertical axis (in Z). The sample holder is capable of supporting circular samples of 300 mm in diameter for example.

Such a head or box for ellipsometry supporting illuminating and analysing arms has the advantage that it further improves the compactness of the ellipsometer according to the invention. Such a head 200 also has the advantage of being connected by optical fibres to distant optical devices (source, detector, spectrograph, processing means, . . . ) which are interchangeable and can be multiplexed.

The means for displacement of the head 200 in translation in X and/or in Y, and/or in Z, respectively 240, 250 and 260 can be means with belts, endless screws or equivalents.

The travel in X is for example of the order of 300 mm, in Y of the order of 500 mm and in Z of the order of 100 mm.

The head 200 and the sample holder 18 as well as the means for displacement of the head are preferably disposed on a plate 270.

As a variant, the ellipsometer according to the invention can comprise another optical head 201 (FIG. 16C) similar to the optical head 200 and capable of being displaced close to the optical head 200 in order to produce another ellipsometry measurement close to the measurement produced by the optical head 200.

Quite clearly, other configurations are possible with the elements as described with reference to FIGS. 1 to 16.

The invention claimed is:

1. Spectroscopic ellipsometer of the type comprising:
   a source capable of emitting a broadband beam;
   a polariser to polarise the broadband beam and to produce a polarised incident beam capable of illuminating a spot on a sample according to at least one chosen angle of incidence;
   an analyser to receive the beam reflected by the sample thus illuminated and to produce an output beam in response to the reflected beam;
   a detector to convert the output beam into an output signal;
   processing means to process the output signal and to determine the changes of phase and of amplitude of the state of polarisation of said output beam caused by the reflection of the polarised incident beam on the sample;
   one of a reflecting optical element and a refracting optical element disposed between the source and the sample and capable of focusing the incident beam according to said spot; and
   the other of the reflecting optical element and the refracting optical element disposed between the sample and the detector in order to focus said reflected beam to dispose the one of the reflecting optical element and the refracting optical element at a first side of said spot and to dispose the other of the reflecting optical element and the refracting optical element on a second side of said spot and thus to dispose the source and the detector on a same one of the first side and the second side of said spot.

2. Eilipsometer as claimed in claim 1, the sample is illuminated according to a large angle of incidence with respect to the normal to the sample.

3. Ellipsometer as claimed in claim 1 or in claim 2, wherein one of the incident beam and the reflected beam has a small angle of incidence with respect to the normal to the reflecting optical element whilst said one of the incident beam and the reflected beam is substantially normal to the refracting optical element.

4. Ellipsometer as claimed in claim 1, further comprising an optical fibre capable of connecting the analyser to an optical device of the type belonging to the group formed by a detector, spectrograph, spectrometer, interferometer and the like.

5. Ellipsometer as claimed in claim 4, wherein the refracting optical element is a first refracting optical element, the ellipsometer further comprising a second refracting optical element disposed between the analyser and an inlet of the optical fibre, the second refracting optical element being capable of focusing the output beam emitted by the analyser into the inlet of the optical fibre.

6. Ellipsometer as claimed in claim 4, wherein the optical fibre is a first optical fiber, the ellipsometer further comprising a second optical fibre capable of connecting the source to the polariser.

7. Ellipsometer as claimed in claim 1, wherein the refracting optical element is a lens of the simple or compound transmitting lens type.

8. Ellipsometer as claimed in claim 5, wherein the second refracting optical element is a lens of the simple or compound transmitting lens type.

9. Ellipsometer as claimed in claim 1, wherein the refracting optical element comprises an aperture capable of allowing the polarised incident beam to pass through if the refracting optical element is disposed between the source and the target and of collecting the reflected beam if the refracting optical element is disposed between the target and the detector.

10. Ellipsometer as claimed in claim 1, further comprising a compensating optical element disposed between the polariser and the analyser upstream or downstream of the sample according to the direction of propagation of the light.

11. Ellipsometer as claimed in claim 1, further comprising a blocking optical element disposed upstream or downstream of the polariser according to the direction of propagation of the light.

12. Ellipsometer as claimed in claim 1, further comprising a blocking optical element disposed upstream or downstream of the first refracting optical element.

13. Ellipsometer as claimed in claim 1, further comprising a blocking optical element disposed upstream of the analyser.

14. Ellipsometer as claimed in claim 10 or in claim 11, wherein the compensating optical element is disposed between the polariser and the blocking element.

15. Ellipsometer as claimed in claim 10 or in claim 13, wherein the compensating optical element is disposed between the blocking optical element and the analyser.

16. Ellipsometer as claimed in claim 1, wherein the refracting element is disposed downstream of the analyser following the direction of propagation of the light.

17. Ellipsometer as claimed in claim 1, wherein the polariser is disposed downstream of the reflecting element following the direction of propagation of the light.

18. Ellipsometer as claimed in claim 1, further comprising a dispersing element mounted downstream of the analyser following the direction of propagation of the light.

19. Ellipsometer as claimed in claim 1, further comprising an interferometer disposed upstream of the polariser following the direction of propagation of the light.

20. Eilipsometer as claimed in claim 1, wherein the polariser and optical elements associated with said polariser as well as the analyser and optical elements associated with said analyser are placed in one and the same optical head.

21. Ellipsometer as claimed in claim 20, wherein the optical head is movable in translation according to the axis X and/or Y in order to displace the incident beam on the sample longitudinally and/or laterally.

22. Ellipsometer as claimed in claim 20, wherein the optical head is movable according to the axis Z in order to displace the incident beam on the sample in height.

23. Ellipsometer as claimed in claim 1, further comprising a fixed sample holder.

24. Ellipsometer as claimed in claim 1, further comprising a sample holder which is movable in X, Y and/or Z and/or in rotation about an axis in Z.

25. Ellipsometer as claimed in claim 1, further comprising a window disposed in a plane substantially parallel to the surface of the sample and through which the incident beam and the reflected beam pass with oblique incidence.

26. Ellipsometer as claimed in claim 20, further comprising another optical head capable of being displaced close the optical head in order to permit another ellipsometry measurement close to the measurement produced by the optical head.

27. Ellipsometer as claimed in claim 7, wherein the refracting optical element comprises a minimal polarising effect and is capable of forming an achromatic assembly with associated optical units.

28. Ellipsometer as claimed in claim 8, wherein the second refracting optical element comprises a minimal polarising effect and is capable of forming an achromatic assembly with associated optical units.

* * * * *

UNITED STATES PATENT AND TRADEMARK OFFICE
CERTIFICATE OF CORRECTION

PATENT NO. : 7,230,701 B2
APPLICATION NO. : 10/333415
DATED : June 12, 2007
INVENTOR(S) : Jean-Louis Stehle et al.

It is certified that error appears in the above-identified patent and that said Letters Patent is hereby corrected as shown below:

On the Title Page

| | |
|---|---|
| (57) Abstract | Delete Abstract as listed, then - Insert --The invention concerns a spectroscopic ellipsometer comprising: a source (2) capable of emitting a broadband ray (4), a polarizer (10) for polarizing the broadband beam (4), and for producing a polarised incident beam (12) adapted to illuminate a sample (16) according to at least a selected angle; an analyzer (24) for receiving the beam reflected (20) by the illuminated sample (16) and for producing an output beam (28) in response to said reflected beam (20); and at least a reflecting optical element (14) arranged between the source (2) and the sample (16) and/or between the sample (16) and the sensor, and capable of focusing the incident beam (12) and/or the reflected ray (20) according to a selected spot. The ellipsometer further comprises at least a first refracting element (22) arranged between the sample (16) and the sensor and/or between the source (2) and the sample (16) to collect and focus said reflected beam and/or said incident beam, thereby enabling to provide at least a refracting element (22) and a reflecting element (14) on either side of the sample (16) and hence to place the source and the sensor on the same side relative to said spot.-- |

In the Claims

| | |
|---|---|
| Column 9, line 40, Claim 2 | Delete "Eilipsometer", Insert --Ellipsometer-- |
| Column 9, line 40, Claim 2 | Before "the sample", Insert --wherein-- |
| Column 9, line 58, Claim 5 | Delete "flbre", Insert --fibre-- |

UNITED STATES PATENT AND TRADEMARK OFFICE
CERTIFICATE OF CORRECTION

PATENT NO. : 7,230,701 B2
APPLICATION NO. : 10/333415
DATED : June 12, 2007
INVENTOR(S) : Jean-Louis Stehle et al.

It is certified that error appears in the above-identified patent and that said Letters Patent is hereby corrected as shown below:

Column 10, line 13, Claim 10    Delete "analyser",
Insert --analyser,--

Column 10, line 54, Claim 23    Delete "Eilipsometer",
Insert --Ellipsometer--

Column 10, line 66, Claim 26    After "close",
Insert --to--

Signed and Sealed this

Twenty-fourth Day of June, 2008

JON W. DUDAS
*Director of the United States Patent and Trademark Office*